United States Patent
Corn et al.

(10) Patent No.: US 10,006,085 B2
(45) Date of Patent: Jun. 26, 2018

(54) NANOSTRUCTURED ARRAYS ON FLEXIBLE POLYMER FILMS

(71) Applicant: The Regents of the University of California, Oakland, CA (US)

(72) Inventors: Robert M. Corn, Corona del Mar, CA (US); Mana Toma, Irvine, CA (US); Gabriel Loget, Irvine, CA (US); Han Wai M. Fung, Irvine, CA (US)

(73) Assignee: The Regents of The University Of California, Oakland, CA (US)

( * ) Notice: Subject to any disclaimer, the term of this patent is extended or adjusted under 35 U.S.C. 154(b) by 0 days. days.

(21) Appl. No.: 14/532,861

(22) Filed: Nov. 4, 2014

(65) Prior Publication Data
US 2015/0126393 A1    May 7, 2015

Related U.S. Application Data

(60) Provisional application No. 61/899,805, filed on Nov. 4, 2013.

(51) Int. Cl.
*C12Q 1/68* (2018.01)
*C12Q 1/6876* (2018.01)
*C12Q 1/6825* (2018.01)
*C12Q 1/6883* (2018.01)
*C12Q 1/6886* (2018.01)
(Continued)

(52) U.S. Cl.
CPC .......... *C12Q 1/6876* (2013.01); *C09D 5/00* (2013.01); *C09D 5/006* (2013.01); *C12Q 1/6825* (2013.01); *C12Q 1/6883* (2013.01); *C12Q 1/6886* (2013.01); *G02B 17/002* (2013.01);
(Continued)

(58) Field of Classification Search
None
See application file for complete search history.

(56) References Cited

U.S. PATENT DOCUMENTS 4,869,714 A * 9/1989 Deininger ............. A61F 2/0077
204/192.34
5,714,359 A * 2/1998 Bowlin .................. A61F 2/062
435/173.1
(Continued)

FOREIGN PATENT DOCUMENTS

EP    1679088 A2    7/2006
EP    2275842 A1    1/2011
(Continued)

OTHER PUBLICATIONS

Jeong et al "Hybrid silicon nanocone-polymer solar cells" Nano Letters, Apr. 30, 2012, 12: 2971-2976.*
(Continued)

*Primary Examiner* — Betty J Forman
(74) *Attorney, Agent, or Firm* — Accelerator AIX; Sean D. Senn

(57) ABSTRACT

The present invention relates to nanocones and nanomaterials. In one embodiment, the present invention provides a method of fabricating an array of nanostructures on a flexible film, comprising self-assembling a layer of particles on a film, and fabricating an array of nanostructures by etching and/or modifying the film. In another embodiment, the present invention provides a microarray comprising a nanomaterial comprising a film configured for an array of one or more nanocones.

10 Claims, 17 Drawing Sheets

(51) Int. Cl.
  *C09D 5/00* (2006.01)
  *G02B 17/00* (2006.01)
(52) U.S. Cl.
  CPC . *C12Q 2600/178* (2013.01); *Y10T 428/24479* (2015.01); *Y10T 428/24612* (2015.01)

(56) References Cited

U.S. PATENT DOCUMENTS

| | | | |
|---|---|---|---|
| 6,849,558 | B2 | 2/2005 | Schaper |
| 7,056,455 | B2 | 6/2006 | Matyjaszewski et al. |
| 7,067,328 | B2 | 6/2006 | Dubrow et al. |
| 7,242,469 | B2 | 7/2007 | Wang et al. |
| 7,258,731 | B2 | 8/2007 | D'Urso et al. |
| 7,491,628 | B2 | 2/2009 | Noca et al. |
| 7,956,525 | B2 | 6/2011 | Armitage et al. |
| 8,073,299 | B2 | 12/2011 | Taghizadeh et al. |
| 8,455,048 | B1 | 6/2013 | Fan et al. |
| 8,553,333 | B2 | 10/2013 | Chang et al. |
| 8,974,889 | B2 | 3/2015 | Bulliard et al. |
| 2003/0134433 | A1 | 7/2003 | Gabriel et al. |
| 2005/0191419 | A1 | 9/2005 | Helt |
| 2006/0184251 | A1 | 8/2006 | Zhang et al. |
| 2007/0120095 | A1 | 5/2007 | Gruner |
| 2010/0216023 | A1 | 8/2010 | Wei et al. |
| 2010/0219562 | A1* | 9/2010 | Sun .................. A61L 31/04 264/334 |
| 2010/0319579 | A1 | 12/2010 | Shay et al. |
| 2011/0285992 | A1* | 11/2011 | Biris .................. C03C 17/006 356/301 |
| 2013/0148194 | A1* | 6/2013 | Altug .................. G01N 21/658 359/350 |
| 2013/0298977 | A1* | 11/2013 | Chen .................. B82Y 30/00 136/255 |
| 2014/0010994 | A1 | 1/2014 | Choi et al. |

FOREIGN PATENT DOCUMENTS

| | | | |
|---|---|---|---|
| EP | 2468884 | A2 | 6/2012 |
| WO | WO201206122266 | * | 5/2012 |
| WO | 2014011294 | A2 | 1/2014 |

OTHER PUBLICATIONS

Ye et al "Two-dinensionally patterned nanostructures based on monolayer colloidal crystals: controllable fabrication, assembly and applications" Nano Today, 2011, 6: 608-631.*
Sardella et al "Nano-structured cell-adhesive and cell-repulsive plasma-deposited coatings: chemical and topographical effects on keratinocyte adhesion" Plasma Processes and Polymers, 2008, 5: 540-551.*
Szabo et al "Surface-enhanced Raman scattering from an etched polymer substrate" Anal. Chem. 1997, 69: 2418-2425.*
Kim, Dae-Hyeong, et al.; Inorganic Semiconductor Nanomaterials for Flexible and Stretchable Bio-Integrated Electronics. NPG Asia Materials; Apr. 2012.
Wang, Zhenxing, et al.; A Flexible UV Nanosendor Based on Reduced Graphene Oxide Decorated ZnO Nanostructures. Nanoscale; 2012; 4: 2678.
Jeong, Sangmoo, et al.; Hybrid Silicon Nanocone-Polymer Solar Cells; American Chemistry Society Nano Letters; 2012; 2971-2976.
Shen, Yangping, et al.; Mechanism and Growth of Flexible ZnO Nanostructure Arrays in a Facile Controlled Way; Journal of Nanomaterials, vol. 2011.
Brunner et al., Antireflective "Moth-Eye" Structures on Tunable Optical Silicone Membranes, Journal for Biomedical Optics (2012), pp. 4370-4376, 51(19).
Chen et al., Ultrahigh Throughput Silicon Nanomanufacturing by Simultaneous Reactive Ion Synthesis and Etching, ACS Nano (Sep. 21, 2011), pp. 8002-8012, 5(10).
Choi et al., Colloidal Lithographic Nanopatterning via Reactive Ion Etching, Journal of American Chemical Society (2004), pp. 7019-7025, 126.
Chung et al., Large Area Flexible SERS Active Substrates Using Engineered Nanostructures, Nanoscale (May 31, 2011), pp. 2903-2908, 3.
De Angelis et al., 3D Hollow Nanostructure as Building Blocks for Multifunctional Plasmonics, Nano Letters (2013), pp. 3553-3558, 13.
D'Urso et al., Emergence of SuperHydrophobic Behavior on Vertically Aligned Nanocone Arrays, Applied Physics Letters (Jan. 22, 2007), 90, 044102.
Fuji et al., Increase in the Extraction Efficiency of GaN-Based Light-Emitting Diodes Via Surface Roughening, Applied Physics Letters (Feb. 9, 2004), pp. 855-857, 84(6).
Garnett et al., Light Trapping in Silicon Nanowire Solar Cells, Nano Letters (Jan. 28, 2010), pp. 1082-1087, 10 (3).
Horrer et al., Nanosphere Lithography: Parallel Fabrication of Plasmonic Nanocone Sensing Arrays, Small Nano Micro (2013), pp. 3987-3992, 9(23).
Kontio et al., Nonoimprint Fabrication of Gold Nanocones With ~10nm Tips for Enhanced Optical Interactions, Optics Letters (Jul. 1, 2009), pp. 1979-1981, 34(13).
Lee et al., ZnO Nanostructures as Efficient Antireflection Layers in Solar Cells, Nano Letters (Apr. 17, 2008), pp. 1501-1505, 8(5).
Pillai et al., Surface Plasmon Enhanced Silicon Solar Cells, Journal of Applied Physics (May 7, 2007), p. 101, 093105-1.
Pogodin et al., Biophysical Model of Bacterial Cell Interactions With Nano-Patterned Cicada Wing Surfaces, Biophysics Journal (2013), pp. 835-840, 104(4).
Sondergaard et al., Plasmonic Black Gold by Adiabatic Nanofocusing and Absorption of Light in Ultra-Sharp Convex Grooves, Nature Communications (Jul. 24, 2012), pp. 1-6, 3(969).
Su et al., Tuning Surface Wettability of InxGa(1−x)N Nanotip Arrays by Phosphonic Acid Modification and Phosphonic Acid Modification and Photoillumination, Langmuir (2011), pp. 13220-13225, 27(21).
Tiwari et al., Ordered Silicon Nanocones as a Highly Efficient Platinum Catalyst Support for Direct Methanol Fuel Cells, Journal of Power Sources (2008), pp. 510-514, 182.
Zhu et al., Nanodome Solar Cells with Efficient Light Management and Self-Cleaning, Nano Letters (Nov. 5, 2009), pp. 1979-1984, 10.
Zhu et al., Optical Absorption Enhancement in Amorphous Silicon Nanowire and Nanocone Arrays, Nano Letters (2009), pp. 279-282, 9(1).

* cited by examiner a) Etching time: 3 min b) Etching time: 6 min c) Etching time: 12 min

NANOSTRUCTURED ARRAYS ON FLEXIBLE POLYMER FILMS

CROSS-REFERENCE TO RELATED APPLICATIONS

The present application claims the benefit of priority under 35 U.S.C. § 119(e) of provisional application Ser. No. 61/899,805 filed Nov. 4, 2013, the contents of which are hereby incorporated by reference.

GOVERNMENT RIGHTS

The U.S. Government has a paid-up license in this invention and the right in limited circumstances to require the patent owner to license others on reasonable terms as provided for by the terms of Grant No. CHE-1057638 awarded by the National Science Foundation (NSF).

FIELD OF THE INVENTION

The present invention relates to hydrophobic and anti-reflective surfaces and more particularly to nanostructured flexible surfaces.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

There are a variety of materials and types of surfaces that may be incorporated in devices. Hydrophobic surfaces bind very weakly with water, which makes drops of water "bead up" on the surface. A hydrophobic surface generally has a water contact angle greater than 90°. Hydrophobic and superhydrophobic surfaces are very important for the fabrication of non-sticky and self-cleaning surfaces. Anti-reflective materials are usually used as coatings on the surface of lenses or other devices to reduce reflections. They are very important in the fields of optics, photovoltaics and military use. Anti-reflective materials can improve the efficiency of the system by reducing the light loss in optics and photovoltaics and can also be used as protection against laser targeting in military applications.

Arrays of nanostructures organized on surfaces are interesting because they provide excellent surface properties such as: superhydrophobicity, anti-reflectivity, enhanced catalytic activity, surface plasmon resonance activity, which are essential for very important applications including biosensors, solar cells, self-cleaning surfaces and anti-reflective coating. A technology to functionalize desired surfaces with these nanostructures is urgently demanded for medical diagnostics, energy industries and military industries and even for every day's life objects (for example, car, clothes, etc.). The problem is that these objects have various and complex shapes, and thus, their coating with such ordered nanostructures is currently difficult since it requires the use of very costly and time consuming technologies.

BRIEF DESCRIPTION OF THE FIGURES

Exemplary embodiments are illustrated in referenced figures. It is intended that the embodiments and figures disclosed herein are to be considered illustrative rather than restrictive.

SUMMARY OF THE INVENTION

Figure 1:
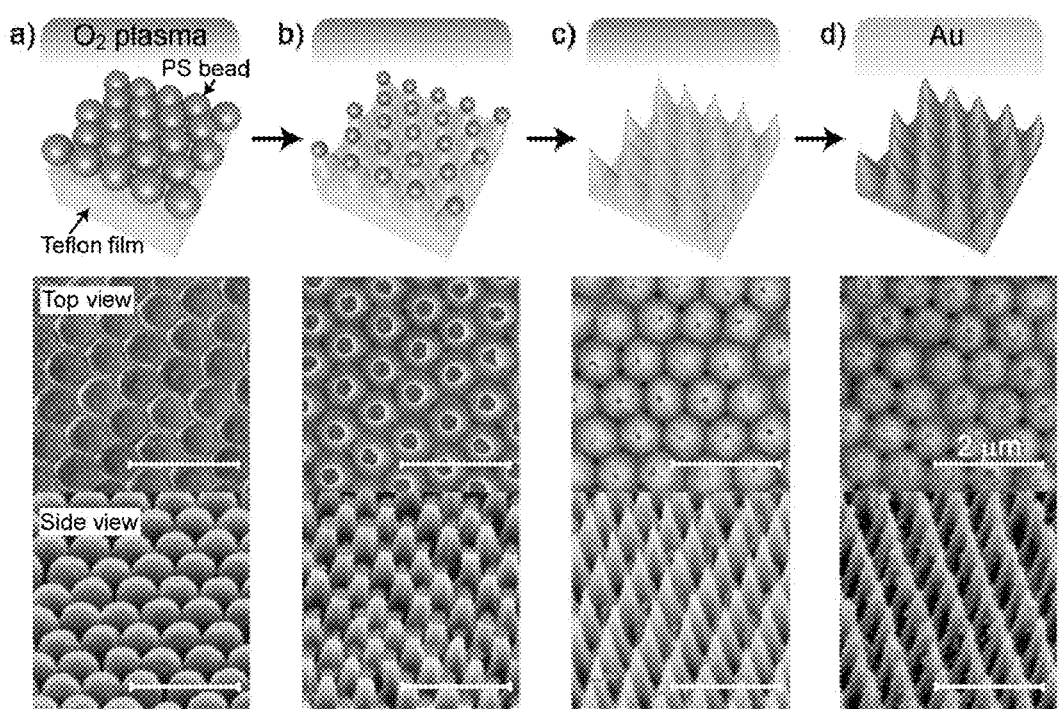
FIG. 1 depicts, in accordance with embodiments herein, schematic illustration of the fabrication process (top row) and colored SEM images of the corresponding samples in both top (middle row) and tilted (bottom row) views. a) Fabrication of a PS bead monolayer on a flexible TEFLON film. b-c) Formation of nanocone arrays by simultaneous plasma etching of PS beads and TEFLON film. d) Deposition of gold thin film on the TEFLON nanocone array. In all the SEM images, the scale bars indicate 2 μm.

Various embodiments include a device, comprising a flexible nanomaterial comprising an array of micrometer and/or nanometer sized cones. In another embodiment, the flexible nanomaterial has anti-reflective and/or hydrophobic properties. In another embodiment, the micrometer and/or nanometer sized cones are TEFLON cones. In another embodiment, the flexible nanomaterial further comprises a polymer film. In another embodiment, the flexible nanomaterial is coated with a material comprising metal, semiconductor, oxides, organic, and/or inorganic compounds. In another embodiment, the array serves as a biosensor for detection of multiple polynucleotides. In another embodiment, the multiple polynucleotides includes miRNA molecules. In another embodiment, the detection of multiple polynucleotides can be visualized by the naked eye. In another embodiment, the biosensor is adapted for portability and/or field testing. In another embodiment, the biosensor is adapted for detection of bacteria, contaminated water, or pathogens in crops. In another embodiment, the nanomaterial comprises one or more polynucleotides attached to a TEFLON nanocone array in a configuration to be adsorbed to complementary polynucleotides modified by AuNPs from a target solution.

Other embodiments include a nanomaterial, comprising a film configured for an array of one or more nanocones. In another embodiment, the film is a polymer film. In another embodiment, the one or more nanocones are TEFLON cones. In another embodiment, the one or more nanocones are created from colloidal beads. In another embodiment, the colloidal beads range in size from a few microns to a few tenths of nanometers. In another embodiment, the nanomaterial is fabricated by introducing a monolayer of monodisperse polystyrene beads on top of the film and etching them with a single step oxygen plasma treatment. In another embodiment, the nanomaterial further comprises a coating to provide a physico-chemical characteristic and/or functionality. In another embodiment, the nanomaterial has one or more of the following properties: superhydrophobicity, anti-reflectivity, enhanced catalytic activity, and surface plasmon resonance activity. In another embodiment, the nanomaterial is used in conjunction with one or more of the following applications: biosensors, solar cells, self-cleaning surfaces and anti-reflective coating.

Other embodiments include a method of fabricating an array of nanostructures on a flexible film, comprising self-assembling a layer of particles on a film, and fabricating an array of nanostructures by etching and/or modifying the film. In another embodiment, the film is a polymer film. In another embodiment, the array of nanostructures are further coated by an additional film. In another embodiment, the film is a metal, polymer, oxide, and/or semiconductor. In another embodiment, the film is a TEFLON film. In another embodiment, the array of nanostructures are cone shaped structures. In another embodiment, the cone shaped structures are created using monolayer and/or multilayer of colloidal beads. In another embodiment, the cone shaped structures are created using differentially etching of colloidal beads introduced on a top film surface and a bottom film surface. In another embodiment, the method further comprises controlling optical properties by changing the size of the cone shaped structures, etching condition, and/or coating. In another embodiment, the method further comprises tuning hydrophilicity properties by changing the size of the cone shaped structures, etching condition, and/or coating. In another embodiment, the method further comprises tuning surface conductivity by coating the array of nanostructures with conductive materials. In another embodiment, the nanostructures include nanocups, nanopyramids and/or nanocavities Various embodiments include a method of coating an object with a complex shape, comprising providing an object with a complex shape, and coating the object by fabricating an array of nanostructures on a flexible film on its surface. In another embodiment, the coated object exhibits hydrophobic and anti-reflective properties. In another embodiment, the coated object exhibits one or more of the following properties: hydrophobic properties and/or anti-reflective properties. In another embodiment, the coated object exhibits hydrophobic or anti-reflective.

Other embodiments include a method of diagnosing a disease in an individual, comprising obtaining a sample from an individual, assaying the sample by using a microarray device comprising a flexible nanomaterial comprising an array of micrometer and/or nanometer sized cones, and diagnosing the individual based on the detection of multiple polynucleotides. In another embodiment, the detection of multiple polynucleotides may be visualized by the naked eye. In another embodiment, the detection of multiple polynucleotides is a result of complementary binding between ssDNA-modified AuNPs and ssDNA-modified nanometer sized cones. In another embodiment, the disease is cancer, heart disease, or a neurodegenerative disease.

Various embodiments include a method of detecting a contaminant in a sample, comprising obtaining a sample, assaying the sample by using a microarray device comprising a flexible nanomaterial comprising an array of micrometer and/or nanometer sized cones, and detecting the contaminant based on the detection of one or more polynucleotides. In another embodiment, the detection of one or more polynucleotides may be visualized by the naked eye. In another embodiment, the detection of one or more polynucleotides is a result of complementary binding between ssDNA-modified AuNPs and ssDNA-modified nanometer sized cones. In another embodiment, the contaminant is a bacteria and/or pathogen. In another embodiment, the contaminant is a food and/or crop pathogen.

Other embodiments include a portable device comprising a nanocone surface in a microarray format with a plurality of spots to detect multiple substances simultaneously. In another embodiment, the nanocone surface further comprises one or more gold nanoparticles that are functionalized for assaying. In another embodiment, the nanocone surface is TEFLON. In another embodiment, the multiple substances are one or more chemical agents associated with chemical warfare. In another embodiment, the multiple substances are one or more performance enhancement compounds.

Other features and advantages of the invention will become apparent from the following detailed description, taken in conjunction with the accompanying drawings, which illustrate, by way of example, various embodiments of the invention.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Hornyak, et al., *Introduction to Nanoscience and Nanotechnology*, CRC Press (2008); Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $7^{th}$ed., J. Wiley & Sons (New York, N.Y. 2013); and Sambrook and Russel, *Molecular Cloning: A Laboratory Manual* $4^{th}$ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As disclosed herein, arrays of nanocones organized on surfaces can provide excellent hydrophobicity and anti-reflectivity. However, the great majority of the materials in the public domain containing nanocone arrays is in the form of rigid surfaces and thus cannot be used for coating objects with complex shapes. Flexible materials comprising an array of nanocone would be highly desirable because those materials can be monofunctional (example, exhibiting one of hydrophobic or anti-reflective properties) or multifunctional (example, exhibiting more than one of the properties) and can be used for coating objects, even with complicated shapes.

As further disclosed herein, the inventors fabricated flexible broadband anti-reflective and light absorbing nanostructured gold thin films by gold vapor deposition onto TEFLON films modified with nanocone arrays. The nanostructures were created by the oxygen plasma etching of polystyrene bead monolayers on TEFLON surfaces. The periodicity and height of the nanocone arrays were controlled by the bead diameter and the overall etching time. The gold nanocone arrays exhibited a reflectivity of less than 1% over a wide spectral range (450 to 900 nm) and a wide range of incident angles (0 to 70 deg). This unique optical response is attributed to a combination of diffractive scattering loss and localized plasmonic absorption. In addition to nanocones, periodic nanostructures of nanocups, nanopyramids and nanocavities can be created by the plasma etching of colloidal bilayers. This fabrication method can be used to create flexible nanocone-structured gold thin films over large surface areas ($cm^2$), and could be rapidly incorporated into new technological applications that require wide-angle and broadband anti-reflective coatings.

In one embodiment, the present invention provides a method of fabricating an array of nanostructures on a flexible film, comprising self-assembling a layer of particles on a film, and fabricating an array of nanostructures by etching and/or modifying the film. In another embodiment, the film is a polymer film. In another embodiment, the array of nanostructures are further coated by an additional film. In another embodiment, the film is a metal, polymer, oxide, and/or semiconductor. In another embodiment, the film is a TEFLON film. In another embodiment, the array of nanoparticles are cone shaped structures. In another embodiment, the cone shaped structures are created using monolayer and/or multilayer of colloidal beads. In another embodiment, the cone shaped structures are created using differentially etching of colloidal beads introduced on a top film surface and a bottom film surface. In another embodiment, method further comprises controlling optical properties by changing the size of the cone shaped structures, etching condition, and/or coating. In another embodiment, the method further comprises tuning hydrophilicity properties by changing the size of the cone shaped structures, etching condition, and/or coating. In another embodiment, the method further comprises tuning surface conductivity by coating the array of nanostructures with conductive materials.

In another embodiment, the present invention provides a method of coating an object with a complex shape, comprising providing an object with a complex shape, and coating the object by fabricating an array of nanostructures on a flexible film on its surface. In another embodiment, the coated object exhibits hydrophobic and anti-reflective properties. In another embodiment, the coated object exhibits two or more of the following properties: hydrophobic properties and anti-reflective. In another embodiment, the coated object exhibits hydrophobic or anti-reflective properties.

In one embodiment the present invention provides one or more arrays of micro and/or nanometer-sized structures on flexible TEFLON film. Specifically, cone shaped structures on flexible TEFLON film, which are created by using differentially etching of colloidal beads introduced on top TEFLON film and the TEFLON film underneath, which can lead to material referred to herein as "Material 1." The cones on TEFLON film may be created using monolayer and/or multilayer of colloidal beads. The TEFLON cone arrays may be coated with other materials including metal, semiconductor, oxides and organic or inorganic compounds with an arbitrary thickness, leading to material referred to herein as "Material 2." The TEFLON cones may be created from few microns to few tenths of nanometers sized colloidal beads. The optical properties of the TEFLON cone arrays such as reflectivity and transmittance are controllable by changing the size of the cone, etching condition and coating. The hydrophilicity of the TEFLON cone array surfaces can be tuned by changing the size of the cone, etching condition and coating. The surface conductivity of TEFLON cone arrays can be tuned by coating with conductive materials. The TEFLON nanocone array surface created on flexible TEFLON film is applicable onto arbitrary surfaces even with complicated geometry.

In one embodiment, the present invention is a device comprising a flexible nanomaterial comprising an array of micrometer and/or nanometer sized cones. In another embodiment, the flexible nanomaterial has anti-reflective and/or hydrophobic properties. In another embodiment, the micrometer and/or nanometer sized cones are TEFLON cones. In another embodiment, the flexible nanomaterial further comprises a polymer film. In another embodiment, the flexible nanomaterial is coated with a material comprising metal, semiconductor, oxides, organic, and/or inorganic compounds.

In another embodiment, the present invention provides a nanomaterial comprising a film configured for an array of one or more nanocones. In another embodiment, the film is a polymer film. In another embodiment, the one or more nanocones are TEFLON cones. In another embodiment, the one or more nanocones are created from colloidal beads. In another embodiment, the present invention includes colloidal beads that range in size from a few microns to a few tenths of nanometers. In another embodiment, the nanomaterial is fabricated by introducing a monolayer of monodisperse polystyrene beads on top of the film and etching them with a single step oxygen plasma treatment. In another embodiment, the present invention further comprises a coating to provide a physico-chemical characteristic and/or functionality. In another embodiment, the present invention comprises Material 1 as further described herein. In another embodiment, the present invention comprises Material 2 as further described herein. In another embodiment, the nanomaterial has one or more of the following properties: superhydrophobicity, anti-reflectivity, enhanced catalytic activity, and surface plasmon resonance activity. In another embodiment, the present invention is used in conjunction with one or more of the following applications: biosensors, solar cells, self-cleaning surfaces and anti-reflective coating.

In another embodiment, the nanostructures include nanocups, nanopyramids and/or nanocavities.

As further disclosed herein, the inventors have used a TEFLON nanocone array surface as a novel, and inexpensive to manufacture biosensor that can simultaneously detect multiple miRNAs. Since detection can be visualized with the naked eye, no additional instruments are necessarily needed. In accordance with various embodiments herein, this makes the TEFLON nanocone surface a portable device suitable for field testing in developing nations, and can greatly advance global health efforts. In another embodiment, the device may be used for other non-diseases sensing applications, including detection of bacteria such as in contaminated water supply or pathogens in crops.

Furthermore, as readily apparent to one of skill in the art, the device may be used for any other additional number of applicable purposes and conducive environments and is in no way limited to only field use for developing countries. For example, in one embodiment, the device may be used for military application wherein the nanocones may be used to detect chemical agents in chemical warfare. Or, for example, in another embodiment, the present invention may provide a device as a means to provide a quick and effective testing for the presence or absence of performance enhancing substances in athletes' urine samples.

In one embodiment, the present invention provides a portable version of the device. In another embodiment, the present invention provides a portable device comprising a TEFLON nanocone surface in a microarray format with a plurality number of spots used to detect multiple substances simultaneously, and one or more gold nanoparticles that are functionalized for the appropriate application. In another embodiment, the present invention provides a method of assaying comprising providing a portable device and assaying from a liquid sample that contains a sample of interest. In another embodiment, the assay may be used to diagnose and/or treat a disease or condition. In another embodiment, the disease or condition is cancer, heart disease, and/or neurodegenerative disease.

As readily apparent to one of skill in the art, various embodiments herein may be used to diagnose and/or treat any number of diseases and conditions and is no way limited to only cancer, heart disease or neurodegenerative diseases.

The present invention is also directed to a kit for detection of biomarkers and/or polynucleotides. The kit is useful for practicing the inventive method of diagnosing a disease or detection, as well as fabrication of a device such as a microarray. The kit is an assemblage of materials or components, including at least one of the inventive compositions. Thus, for example, in some embodiments the kit contains a composition including flexible film or nanocones, or compositions including ssDNA, as described above.

The exact nature of the components configured in the inventive kit depends on its intended purpose. For example, some embodiments are configured for the purpose of diagnosing and/or treating a disease, such as heart disease or cancer. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to detect a contaminant. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing AuNP or polynucleotides or modified ssDNA. The packaging material generally has an external label which indicates the contents and/or purpose of the kit and/or its components.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Broadband Anti-Reflective Plasmonic Gold Nanocone Arrays

Flexible broadband anti-reflective and light absorbing nanostructured gold thin films are fabricated by gold vapor deposition onto TEFLON films modified with nanocone arrays. The nanostructures are created by the simultaneous oxygen plasma etching of polystyrene bead monolayers and the TEFLON surfaces underneath. The periodicity and height of the nanocone arrays are controlled by the bead diameter and the overall etching time. The gold nanocone arrays exhibit a reflectivity of less than 1% over a wide spectral range (450 to 900 nm) and a wide range of incident angles (0 to 70 deg); this unique optical response is attributed to a combination of diffractive scattering loss and localized plasmonic absorption. In addition to nanocones, periodic nanostructures of nanocups, nanopyramids and nanocavities can be created by the plasma etching of colloidal bilayers. This fabrication method can be used to create flexible nanocone-structured gold thin films over large surface areas (cm$^2$) and should be rapidly incorporated into new technological applications that require wide-angle and broadband anti-reflective coatings.

Arrays of nanostructures such as nanocones, nanotips, nanopillars and nanowires have attracted great attention recently due to their notable characteristics such as broadband anti-reflection and light trapping properties, strong hydrophobicity and high surface area, with applications in photonic and photovoltaic devices, biological and chemical sensors and self-cleaning surfaces. To date, a variety of nanostructures created from metals, semiconductors, oxides and polymers have been reported. For example, silicon nanostructured arrays are currently studied intensively, as their excellent anti-reflective properties can provide better efficiency in solar cell applications. Noble metal nanostructured arrays are also studied extensively due to their remarkable mass-transfer properties when used as nanoelectrodes and their notable surface plasmon properties. Sharp nanocones and nanotips made with noble metals exhibit strong electromagnetic field enhancement at the tips when they are exposed to a light. This plasmonic field enhancement effect has been employed for surface-enhanced Raman spectroscopy, surface-enhanced fluorescence and secondary harmonic generation. The arrays of metal nanostructures also hold a potential as a blackbody materials due to their broadband anti-reflective and light absorption properties, which are induced by the excitation of localized surface plasmon resonances and their interactive coupling.

Incorporation of the excellent optical properties of metal nanocone arrays into devices and components requires the development of simple, rapid and scalable fabrication methods. Serial, "top-down" fabrication methods such as focused ion beam etching and e-beam lithography have been used to create metallic nanostructures with precise control. However, the fabrication of arrays with these technologies is slow and limited in total obtainable structured area. A parallel "bottom up" approach that combines colloidal lithography and reactive ion etching is an alternative way to fabricate nanocone arrays. By using the colloidal monolayer as an etching mask, large scale fabrication of nanocone arrays can be achieved. However, such processes often require multiple etching steps in order to create the desired nanocone structures.

The inventors demonstrated a new fabrication method for creating two dimensional periodic gold nanocones arrays on flexible TEFLON films. In this approach, a combination of colloidal lithography and oxygen plasma etching is employed. The simultaneous competitive differential etching of polystyrene bead layers and TEFLON films allows us to fabricate nanocones arrays on the centimeter scale with a single etching step. The periodicity and size of nanocone arrays are easily tuned by changing the bead diameter and the etching time. Unique structures such as nanocups, nanopyramids, nanotips and nanocavities arrays can also be created by applying the same differential etching method to colloid bilayers. After depositing a thin gold layer on top of the nanocone arrays, the surface of nanocone arrays exhibits highly hydrophobic properties and the color of the sample turns matte-black indicating that the film has acquired broadband anti-reflection and light absorption properties. Optical measurements reveal that the gold nanocone arrays exhibit low reflectivity (below 1%) and strong absorption (around 90%) at wide angle and wavelength range (450-900 nm).

Figure 2:
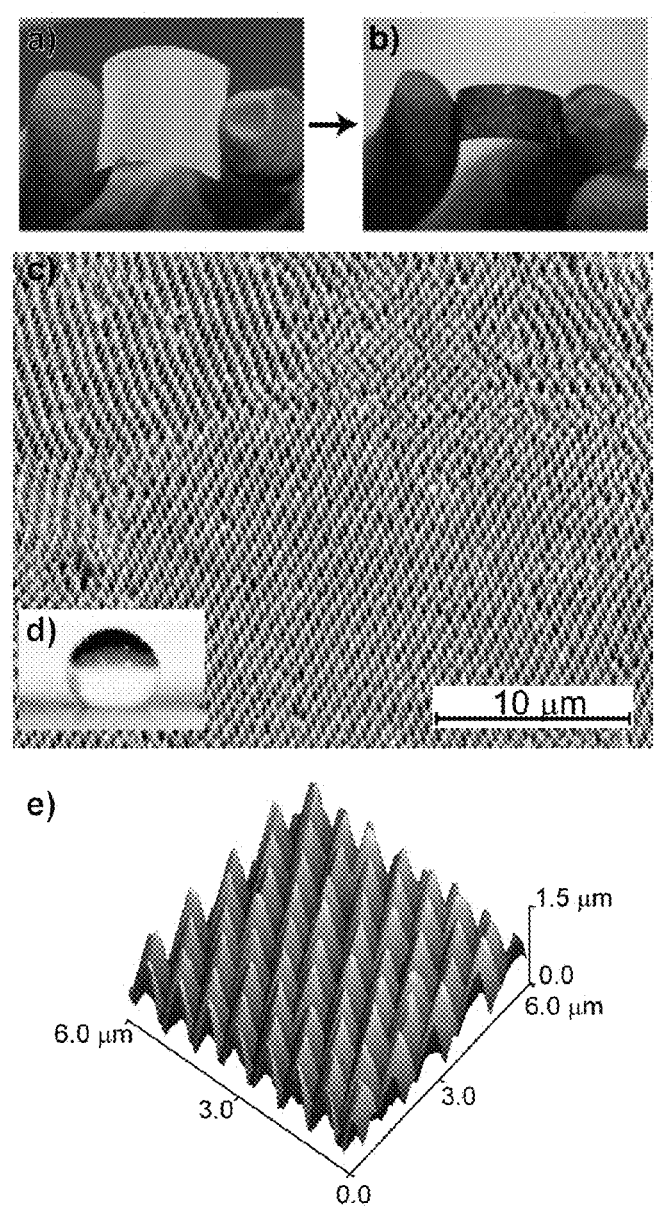
FIG. 2 depicts, in accordance with embodiments herein, photographs of the nanocone arrays on TEFLON film. The photographs show a) before and b) after coating with 50 nm thick gold layer. c) SEM image of the gold nanocone array in tilted view. d) Photograph of a water droplet on gold nanocone array showing the hydrophobicity of the surface. e) Three-dimensional AFM image of the gold nanocone array.
Figure 3:
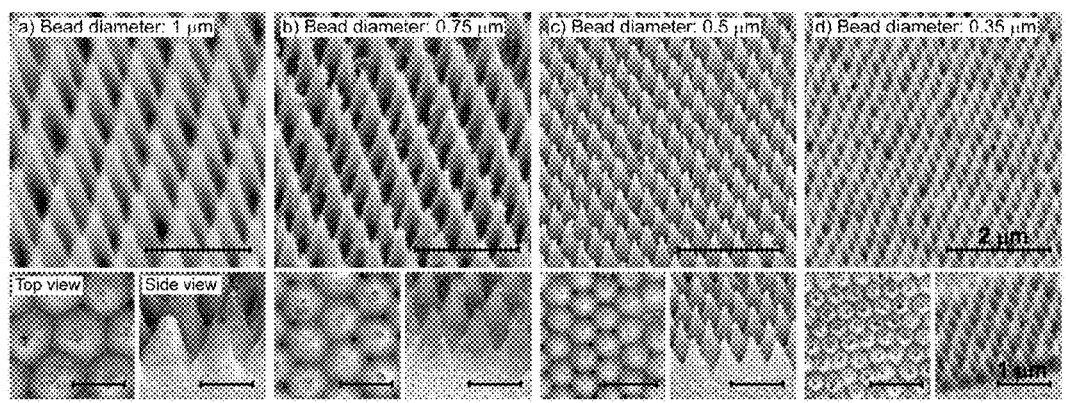
FIG. 3 depicts, in accordance with embodiments herein, SEM images of nanocone arrays fabricated with PS beads with different diameter. The diameter includes a) 1 μm, b) 0.75 μm, c) 0.5 μm and d) 0.35 μm. The top row shows large tilted views. In the bottom row, left and right images show top view and side view of nanocones, respectively. In all the top and bottom SEM images, the scale bars indicate 2 μm and 1 μm, respectively.

The fabrication process of gold nanocone arrays is described in FIG. 1 herein. The colored SEM images in middle and bottom rows show the representative samples at each fabrication steps from top and tilted view, respectively. Firstly, a colloidal monolayer is formed on top of flexible TEFLON film by spincoating a solution of polystyrene (PS) beads with a diameter of 0.75 µm. After drying the solvent, the PS beads assemble in hexagonal packed arrays on the TEFLON film as shown FIG. 1a. The surface is then etched by oxygen plasma. During exposure to the oxygen plasma, the PS beads and the TEFLON film underneath are etched simultaneously and the nanocone structures are created on the TEFLON film (FIG. 1b-c). For a short etching time (3 min), a hybrid structure consisting of shrunk PS beads (in pink) and TEFLON nanopillars (in green) is created (FIG. 1b). As the etching time increases, the PS beads decrease and the heads of nanopillars sharpen. This is illustrated by FIG. 1c herein, obtained for 6 min of etching, which shows that only small PS residues remain on the top of nanocones. Finally, the TEFLON nanocones are coated with a thin gold layer (50 nm thick) by thermal evaporation (FIG. 1d). As it can be observed on these SEM images, the surface roughness increases after the gold evaporation but the nanocones structure is retained. FIG. 2a-b show photographs of a nanocone array (0.75 μm PS beads, 5 min of oxygen plasma etching) before and after coating of the gold thin film, respectively. First, one can note that the flexibility of the TEFLON film is retained after the fabrication process. Second, the color gives important information about the macroscopic optical properties of these nanostructures. As shown in FIG. 2a herein, due to the formation of the nanocone array, the surfaces of TEFLON film turns from glossy transparent to matte-white indicating strong light scattering by the nanostructures. The TEFLON nanocone array exhibited anti-reflective property which is attributed to a gradual effective refractive index changes from air to TEFLON. As shown in FIG. 2b herein, the color of the film becomes matte-black after deposition of gold indicating strong light absorption by gold in addition to anti-reflective property. Moreover, the film becomes conductive after deposition of gold with a measured conductivity of 22 $mS \cdot cm^{-1}$ which suggests that the gold thin film is electrically connected over the whole surface. FIG. 2c herein shows an SEM image presenting a large view of gold nanocone arrays. This SEM image reveals that the nanocone array consists of multiple oriented domains of hexagonally-packed nanocones. The characteristic dimension of single oriented domains is of several tens of micrometers. FIG. 2d shows a photograph of a water drop (10 μl) on the gold nanocone array. The contact angle was measured to be 145°, which is close to a value of a super-hydrophobic surface, 150°. This indicates that the structure of nanocone arrays makes the surface highly hydrophobic in contrast to a plane gold surface (the measured contact angle is 52°), due to the air pockets trapped in the interspaces among nanocones. This structural hydrophobicity of nanocone arrays agrees with previous works. The array structure in a single domain was studied by the atomic force microscopy (AFM) measurement shown in FIG. 2e herein. This AFM image reveals the hexagonally-packed nanocones have a homogenous height of about 1 μm.

A control over the nanocone arrays geometry was done by changing the size of PS beads. FIG. 3a-d show the SEM images of nanocone arrays created with PS beads with different diameters, 1 μm, 0.75 μm, 0.5 μm and 0.35 μm, respectively. The tilted large view, the top view and the side view of gold nanocone arrays are presented in top row, bottom left row and bottom right row, respectively. The nanocone arrays were fabricated with the same $O_2$ plasma etching time and the SEM images of FIG. 3 herein are directly comparable since they were taken with the same magnification. The large tilted views of nanocone arrays clearly show the significant changes in their dimensions and surface densities depending on the bead diameter. The period of the arrays was obtained from the top view SEM images by fast Fourier transform (FFT) analysis. The heights of nanocones were determined by AFM measurements. The period, height and aspect ratio of each nanocone arrays are summarized in Table 1 below. The period and height of nanocone array were found to decrease as the bead diameter decreases. The measured periods are slightly smaller than the expected bead diameter for all samples, which could be explained by the slight difference of bead diameter obtained by dynamic light scattering and SEM measurements. The aspect ratio of nanocones, which is obtained from the height of nanocones divided by the period, was determined to vary from 1.4 to 1.0 with the bead diameter from larger to smaller.

Figure 4:
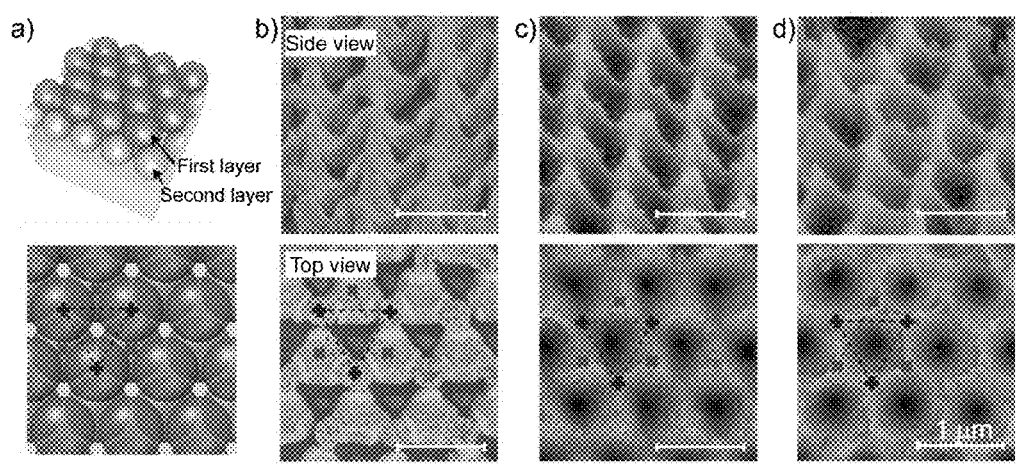
FIG. 4 depicts, in accordance with embodiments herein, various schematic pictures. a) Schematic representation of a colloidal bilayer structure (top: tilted view, bottom: top view). b-d) Colored SEM images of colloidal bilayer structures after 3, 6 and 12 min $O_2$ plasma treatment, respectively. The areas corresponding to the first and second PS beads layers and TEFLON film are colored following the schematic drawing. In all the SEM pictures, crosses indicate the central position of PS beads at first (blue) and second (magenta) layers and the scale bars indicate 1 μm.

In addition to the geometry control of nanocones by the bead diameter, the presented fabrication technique allows the creation of more complicated structures such as nanocup, nanopyramid, nanotip and nanocavity arrays by using bilayers of PS beads. The scheme of a colloidal bilayer structure is shown in FIG. 4a herein. The central positions of PS beads in both top and bottom layers are marked with crosses in the top view image illustrated in bottom row. FIG. 4b-d are colored SEM pictures showing characteristic structures created by using colloidal bilayers (0.75 μm PS beads) with different plasma etching time from 3 to 12 min. For short etching time (3 min), the PS beads in the top layer become smaller but still keep their circular shape, as shown in the top view SEM image in FIG. 4b. The PS beads in the bottom layer form a cup-like shape as a result of simultaneous etching of first and second layers of PS beads. The portions of the TEFLON film that are not protected with colloids are also etched with triangle shape holes. For longer etching time (6 min), the PS beads are totally etched and the TEFLON film forms a hybrid structure of nano-triangle pyramids and nanocavity arrays. As marked in FIG. 4c, the highest peaks correspond to the center position of the bottom colloidal layer, which are the most protected areas against oxygen plasma. The second peaks correspond to the center of the top colloidal layer. Nanocavities are observed at the center of the triangles made by cross marks where the TEFLON film is less protected. When the sample is etched longer (12 min), the nanopyramids become nanotips and the cavities among nanotips enlarge, as presented by FIG. 4d herein.

Figure 5:
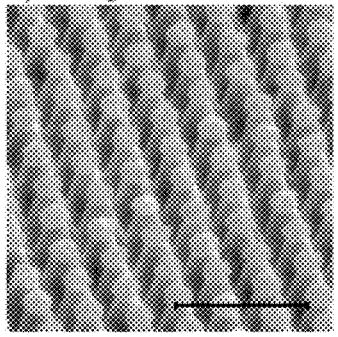
FIG. 5 depicts, in accordance with various embodiments herein, SEM images of gold nanocone arrays (top row) and individual nanocones (left figures in bottom row), and photographs of the samples (right figures in bottom row) corresponding to the SEM images which show color of each sample. In a) to c), all the top SEM images, the scale bars indicate 2 μm and in all the bottom SEM images, the scale bars indicate 1 μm. In all the photographs, the scale bars indicate 1 mm.
Figure 5:
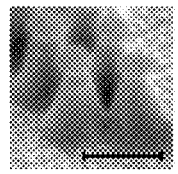
Figure 5:
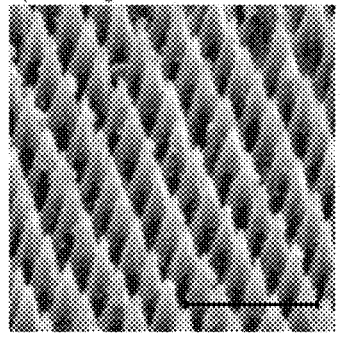
Figure 5:
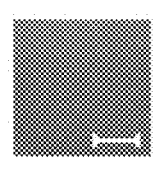
Figure 5:
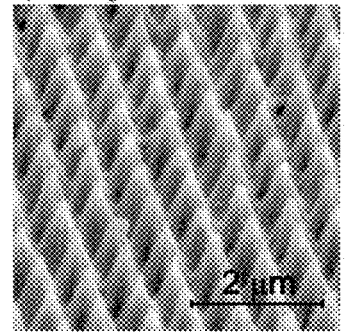
Figure 5:
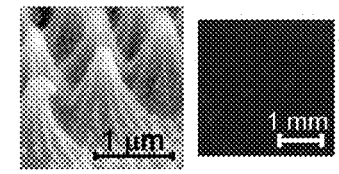

In addition to the fabrication of nanocone arrays and the other structures from a materials science point of view, the inventors focused on the optical properties of gold nanocone arrays. The gold nanocone arrays hold outstanding optical properties which produce their matte-black color (see FIG. 2b herein). Firstly, the color of gold nanocone arrays is controlled by their structure. In the experiment described in FIG. 5, nanocone arrays were fabricated with 0.75 μm PS beads with various oxygen plasma etching times. The fabricated TEFLON nanocone arrays were then coated with 50 nm of gold. FIG. 5a-c show the structures and the corresponding colors depending on the plasma etching time: 3, 6 and 12 min. For 3 min plasma etching, the SEM image shows that the colloidal beads still remained on the top of the cones and the color of the sample is similar to a flat gold film (FIG. 5a). As shown in FIG. 5b herein, the color of the sample becomes black with 6 min plasma etching, as the colloidal beads are completely etched and the tips of nanocones get sharper. The color gets slightly brighter for longer etching time (12 min, FIG. 5c). This phenomenon is attributed to the lower aspect ratio of nanocones compared to that created by 6 min plasma etching.

Figure 6:
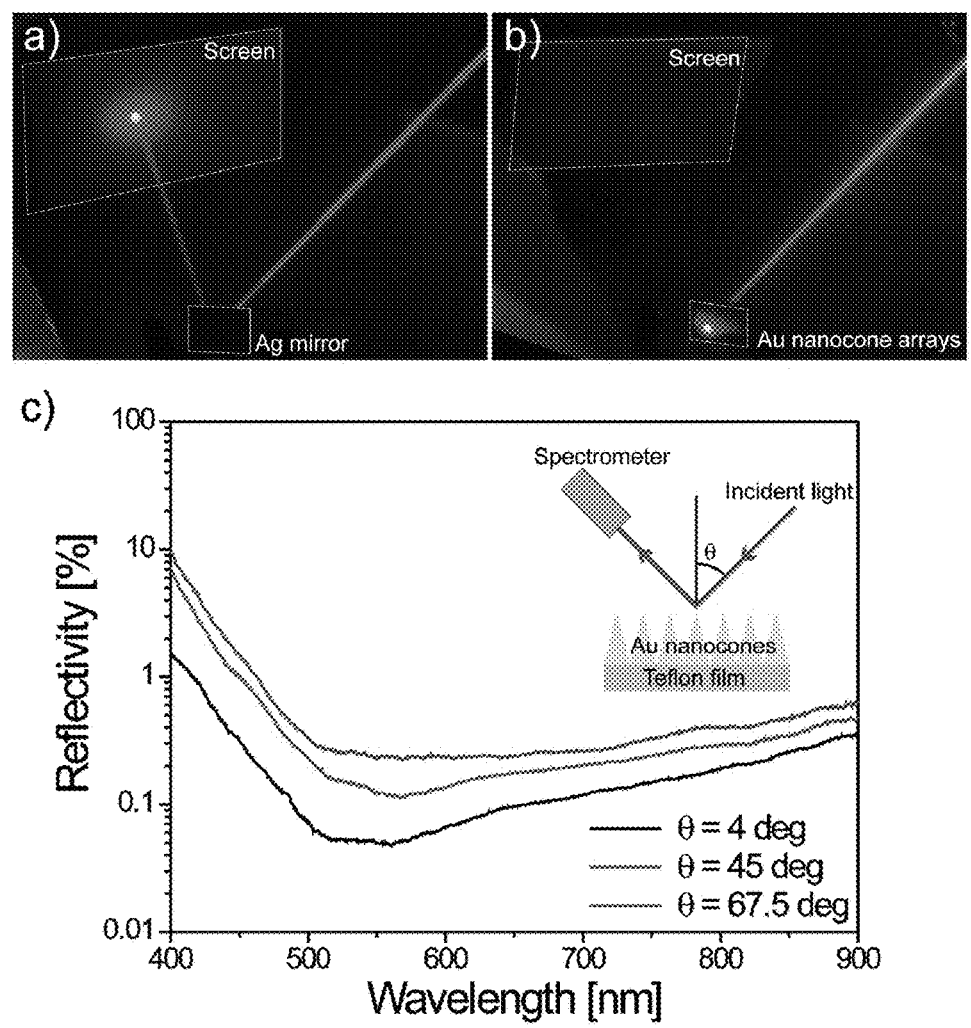
FIG. 6 depicts, in accordance with various embodiments herein, photographs showing the laser beam path reflected by a) a silver mirror and b) a gold nanocone array. c) Reflectivity spectra from gold nanocone arrays at different angles of incidence, 4° (black), 45° (red) and 67.5° (blue). The inserted schematic shows the optical setup used for reflectivity measurement.
Figure 7:
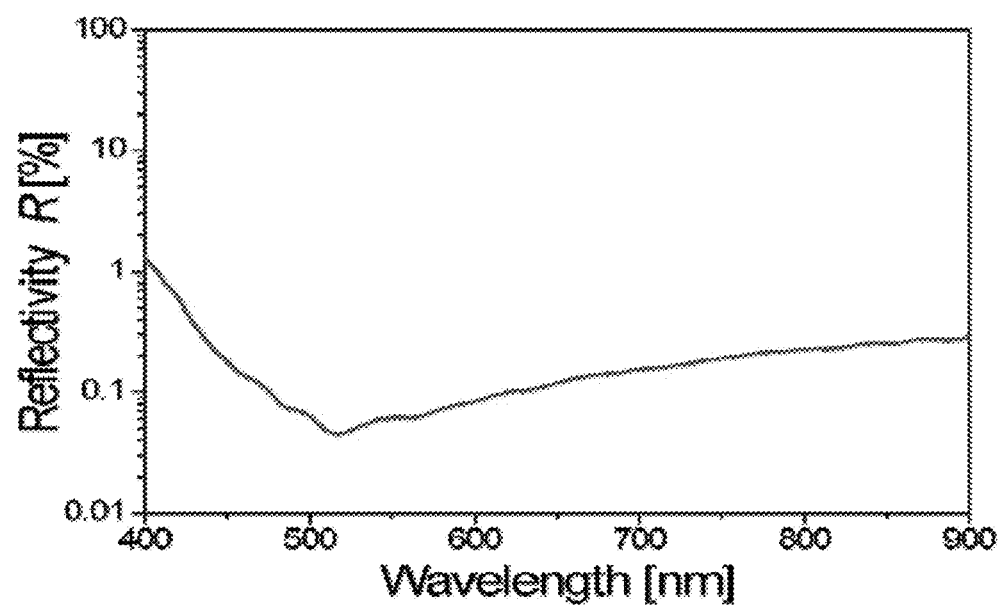
FIG. 7 depicts, in accordance with various embodiments herein, reflectivity spectrum of TEFLON nanocone array at an angle of incidence of 4°. The spectrum is smoothed by averaging over 100 points in order to eliminate the noises.
Figure 8:
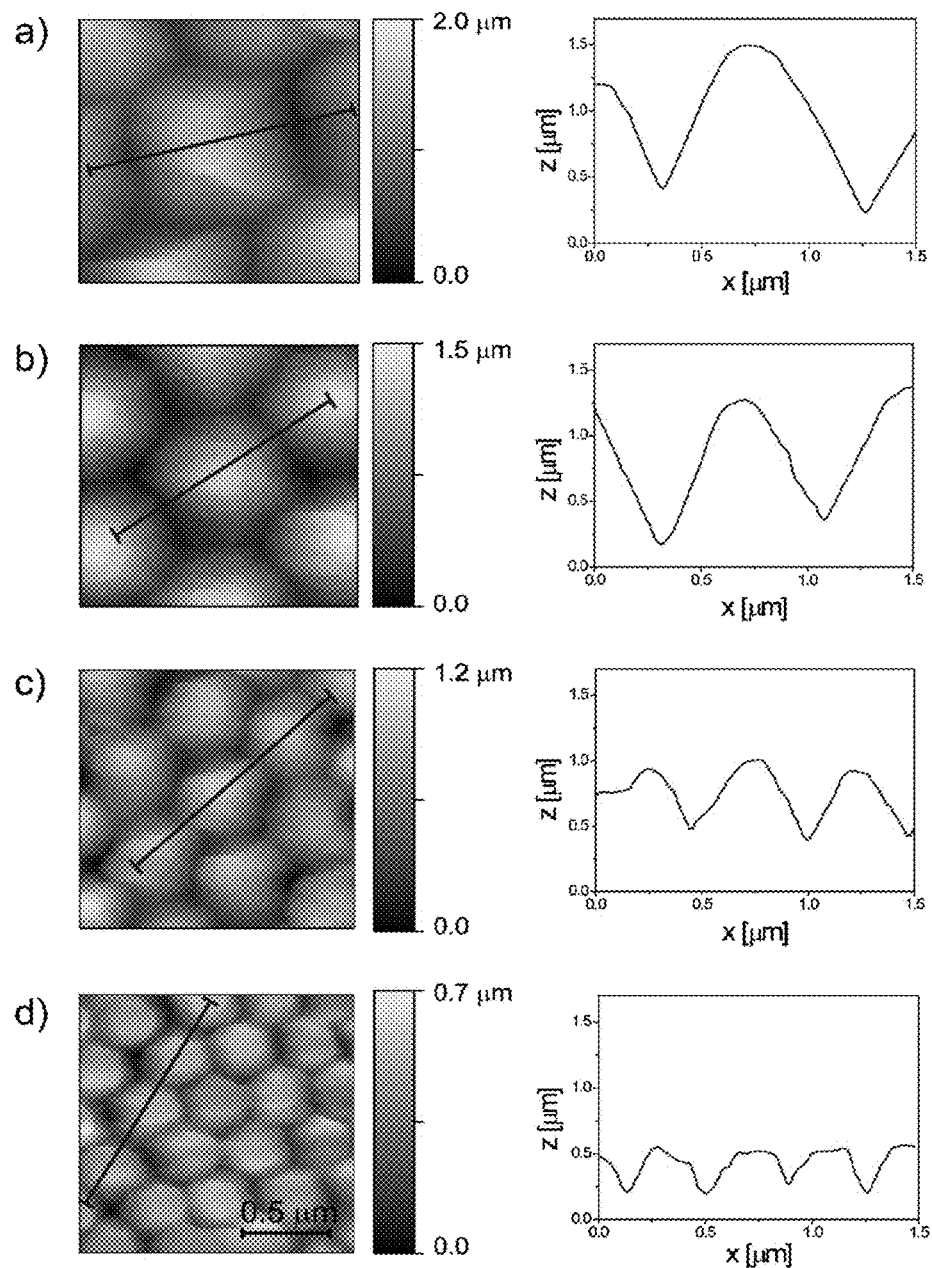
FIG. 8 depicts, in accordance with various embodiments herein, AFM images of gold nanocone arrays. AFM images (left column) and corresponding profiles (right column) of gold nanocone arrays fabricated with (a) 1 μm, (b) 0.75 μm, (c) 0.5 μm and (d) 0.35 μm. The blue lines in AFM images indicate the areas where the profiles are taken.
Figure 9:
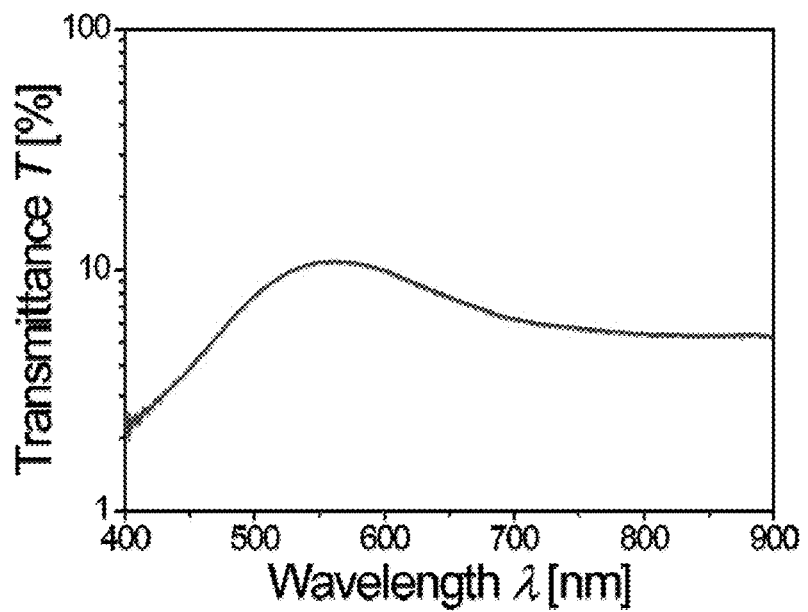
FIG. 9 depicts, in accordance with various embodiments herein, transmittance spectrum of gold nanocone arrays at normal incident. The sample is identical with that used for reflectivity measurement in FIG. 6 herein. The presented spectrum was smoothed by averaging 100 data points in order to eliminate noises.
Figure 10:
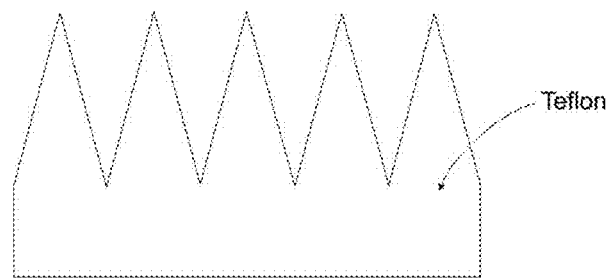
FIG. 10 depicts, in accordance with various embodiments herein, scheme describing material referred to herein as "Material 1," further disclosed herein. The top part of the TEFLON film consists of an array of micrometer or nanometer-sized nanocones.
Figure 11:
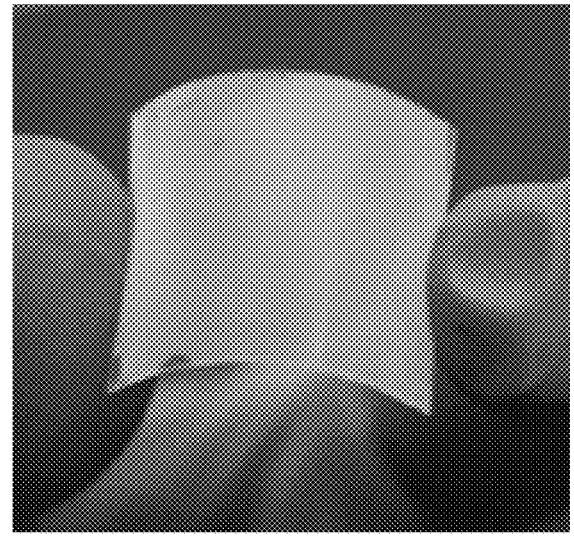
FIG. 11 depicts, in accordance with various embodiments herein, a photograph of Material 1, obtained with polystyrene beads having a diameter of 0.75 micrometer.
Figure 12:
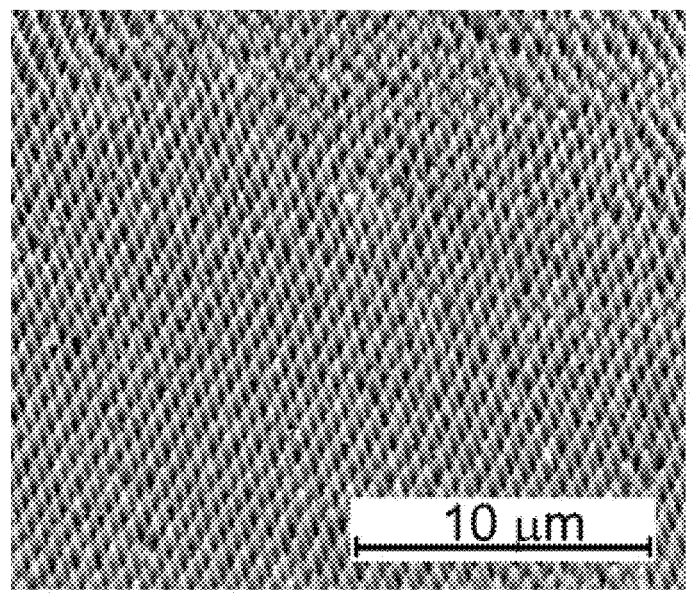
FIG. 12 depicts, in accordance with various embodiments herein, a scanning electron microscopy image of Material 1, obtained with polystyrene beads having a diameter of 0.75 micrometer.
Figure 13:
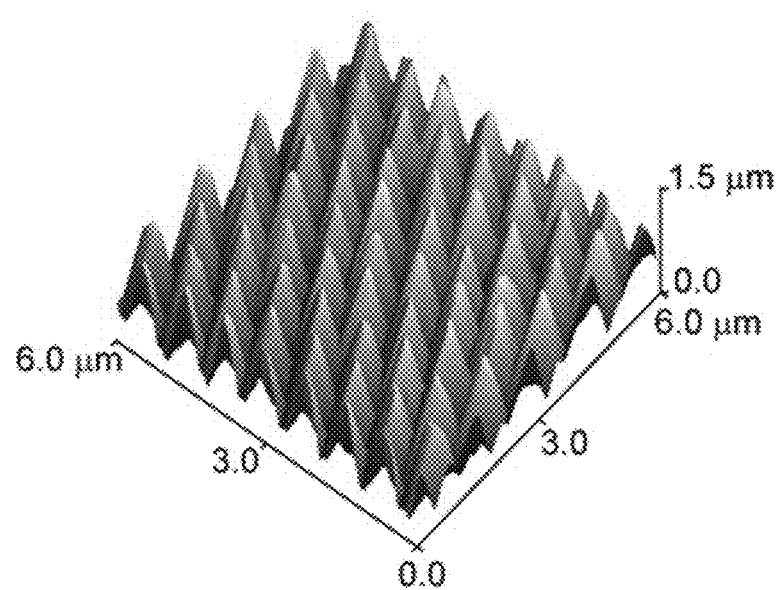
FIG. 13 depicts, in accordance with various embodiments herein, atomic force microscopy image of Material 1, obtained with polystyrene beads having a diameter of 0.75 micrometer.
Figure 14:
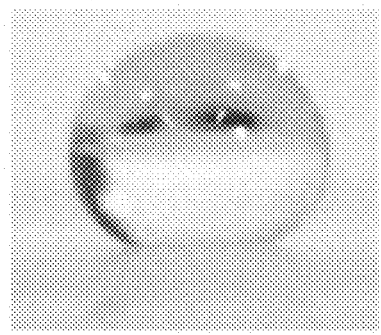
FIG. 14 depicts, in accordance with various embodiments herein, a photograph of a water droplet on Material 1.
Figure 15:
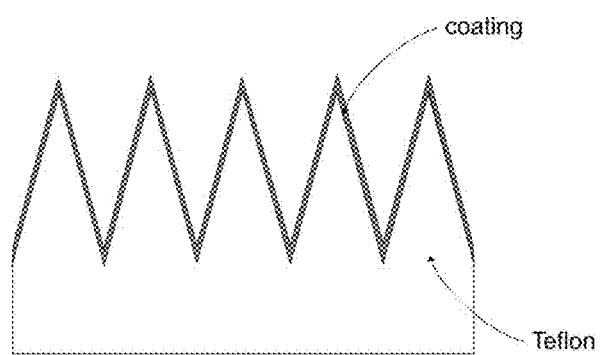
FIG. 15 depicts, in accordance with various embodiments herein, a scheme describing material referred to herein as "Material 2," further disclosed herein. The TEFLON film is covered on the cone size with a coating.
Figure 16:
FIG. 16 depicts, in accordance with various embodiments herein, a photograph of Material 2, obtained with polystyrene beads having a diameter of 0.75 micrometer and a gold coating on the TEFLON cones.
Figure 17:
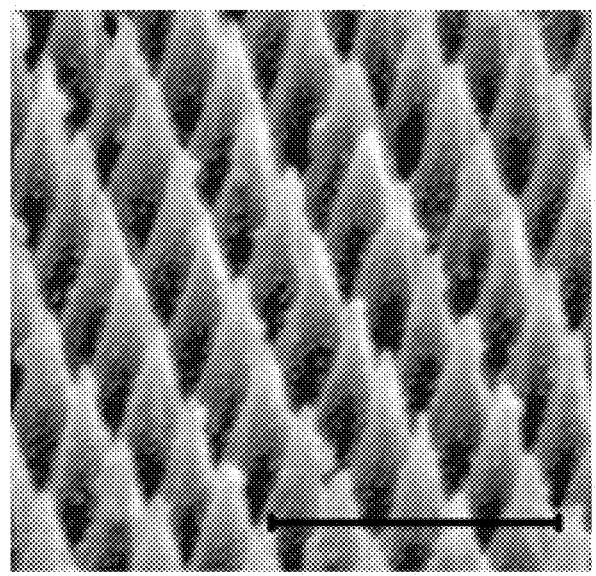
FIG. 17 depicts, in accordance with various embodiments herein, a scanning electron microscopy image of Material 2 obtained with polystyrene beads having a diameter of 0.75 micrometer and a gold coating on the TEFLON cones. The scale bar indicates 2 micrometers.
Figure 18:
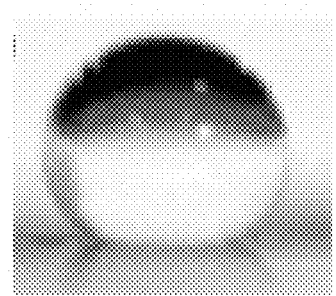
FIG. 18 depicts, in accordance with various embodiments herein, a photograph of a water droplet on Material 2.
Figure 19:
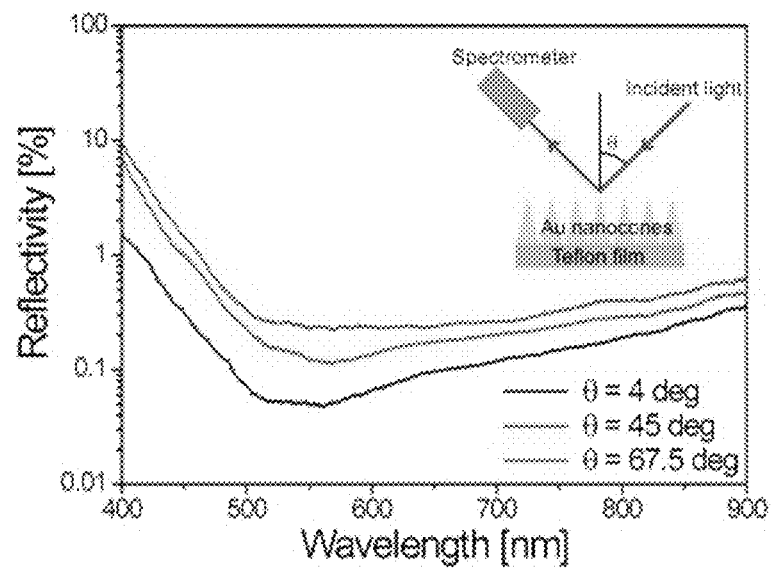
FIG. 19 depicts, in accordance with various embodiments herein, a reflectivity spectrum from Material 2, obtained with polystyrene beads having a diameter of 0.75 micrometer and a gold coating on the TEFLON cones at different angles of incidence.

Furthermore, the inventors investigated the anti-reflective properties of gold nanocone arrays prepared with 0.75 μm PS beads and 6 min plasma etching. FIG. 6a-b show the beam path from a He—Ne laser with a wavelength of 633 nm made incident on and reflected by a flat silver mirror (200 nm thickness) and gold nanocone arrays, respectively. In the case of a gold nanocone array, the photograph clearly shows that almost no light is reflected and no spot is observed on the screen in contrast with the flat silver film that exhibit strong reflection. The wavelength reflectivity spectra from gold nanocone arrays at several angles of incident, 4°, 45° and 67.5° are presented in FIG. 6c herein. The reference spectrum was taken with a silver mirror. When the angle of incident is set to 4°, the reflectivity R from the gold nanocone array is below 1% at whole wavelength range. The minimum reflectivity $R_{min}$=0.05% is observed in a wavelength range between 500 to 550 nm. At 633 nm wavelength, the reflectivity R=0.1% and transmittance T=8% (the transmittance spectrum at normal incident is shown herein). By using a simple equation to determine the absorbance A (A=1−R−T), it is calculated that the gold nanocone array absorbs over 90% of incident light at this wavelength. Even though the reflectivity slightly increases as the angle of incident increases, the reflectivity is kept below 1% for almost whole visible spectrum range above 480 nm in wavelength. This black coloring is attributed to a combination of diffractive scattering loss from the periodic structure and localized plasmonic absorption from the rough gold film (see FIG. 1d herein). Compared to other metallic nanostructures proposed for anti-reflective black silver and black gold, the inventors' gold nanocone arrays exhibit excellent anti-reflective properties with a lower reflectivity at a visible wavelength range.

In conclusion, the inventors have presented an example of a simple two step method for the fabrication of gold nanocone arrays on flexible films which exhibit excellent broadband anti-reflective and light absorption properties as well as high hydrophobicity. The nanocone structures were fabricated by the simultaneous oxygen plasma etching of polystyrene colloidal monolayers and the underlying TEFLON film. They showed that the periodicity and height of nanocone arrays were tunable with the size of colloid and oxygen plasma etching time. Various unique two dimensional arrays with structures including nanocups, nanopyramids and nanotips and nanocavities arrays could also be created by etching colloidal bilayers. After deposition of a thin gold film, the nanocone arrays acquire strong black coloring. Reflectivity measurements revealed that the gold nanocone arrays are strongly anti-reflective (reflectivity below 1%) through the entire visible spectrum and over a wide range of incident angles (0° to 70°). The flexible nature of these films and the ability to fabricate nanocone arrays on large areas opens up new technologic applications for these wide-angle and broadband anti-reflective coatings. The strong absorptive properties of the gold nanocone arrays also suggests their potential application in plasmonic black body and photovoltaic devices. The nanocone arrays may also be applied to superhydrophobic surfaces.

Example 2

Table 1—Bead Diameters, Periods of Arrays, Heights and Aspect Ratios of Nanocones Etched for 6 Min

TABLE 1

| Bead diameter [μm] | Period [μm] | Height [μm] | Aspect ratio |
|---|---|---|---|
| 1.0 | 0.86 ± 0.1 | 1.21 ± 0.1 | 1.4 |
| 0.75 | 0.70 ± 0.07 | 1.01 ± 0.13 | 1.4 |
| 0.5 | 0.45 ± 0.04 | 0.59 ± 0.09 | 1.3 |
| 0.35 | 0.32 ± 0.02 | 0.31 ± 0.05 | 1.0 |

Example 3

Experimental Procedure

Chemicals and Materials:

All the solvents and chemicals were used as received, ethanol was obtained from Sigma-Aldrich, methanol was obtained from J.T. Baker, triton-X-100 (TX100) was purchased from Fischer Scientific. The TEFLON film (thickness 0.005") was obtained from CS hyde Company. The PS beads (Polybead carboxylate, 2.5 w/v %) were purchased from Polyscience. The silver mirrors were prepared by thermal vapor deposition (DV 502-A evaporator, Denton Vacuum) of 200 nm thick silver film on cover slips.

Fabrication of Gold Nanocone Arrays:

Before spincoating PS beads, a TEFLON film was cut into square (typically 1.5×1.5 cm) and cleaned by rinsing with ethanol and MilliQ water followed by plasma cleaning (PDC-32G, Harrick Plasma) for 3 min. A solution of PS beads (1 mL) were centrifuged and transferred to a mixture containing ethanol and methanol with a 2:1 ratio. A surfactant (TX100) was added to the solution at 0.2 vol %. The concentration of PS beads was adjusted to about 5 w/v %. The PS beads were then spin-coated on a cleaned TEFLON film and left at room temperature for few minutes to let the solvent dry. The PS bead/TEFLON surface was etched by $O_2$ plasma (200 mTorr, 50 W, PC2000, South Bay Technology) for the desired time. The surface was finally coated with 50 nm of gold by thermal evaporation.

SEM and AFM Characterization:

For the SEM characterization of the TEFLON nanocone arrays, a thin layer of Pd was previously sputtered by ion beam sputter deposition (IBS/e, South Bay Technology) on the surface in order to ensure a good electrical conduction. The gold nanocone arrays were characterized without coating. A FEI Quanta 3D FEG SEM was used for imaging the surfaces. The tilted views were performed using an angle of 52°. The colored SEM pictures were obtained using the GIMP 2.6 software. The Fast Fourier Transform (FFT) analysis of SEM image is carried out by using ImageJ. The AFM characterization was achieved with an Asylum Research MFP-3D. The analysis of AFM images were performed by using Gwyddion.

Optical Measurements:

The sample (the film with nanocone arrays or silver mirror) is attached to a glass slide by using refractive index matching oil then installed onto a rotation stage. For the observation of the laser beam path reflected from gold nanocone arrays and silver mirrors, a light beam from HeNe laser (1125/P, JDSU) at wavelength of 633 nm was directed incident to the surfaces and the reflected light was hit on a white screen. Smokes from dry ices in water were used in order to visualize the laser pathway. The photographs were taken in the dark with a Canon 40D camera. For reflectivity and transmittance measurements, a halogen ramp was used as a white light source. The emitted light from a halogen light is coupled into an optical fiber (M25L01, Thorlabs), collimated with an achromatic lens (f=50 mm, AC254-050-A-ML, Thorlabs) then made incident to the sample surface. The reflected of transmitted light is coupled into an optical fiber (P1000-2-VIS/NIR, Ocean Optics) with an achromatic lens (f=30 mm, AC254-030-A-ML, Thorlabs) then characterized with a UV-Vis spectrometer (USB4000, Ocean Optics). For the reflectivity measurement, a silver mirror is used as a reference.

Example 4

Nanocone Arrays on Flexible Polymer Film

In accordance with various embodiments herein, the present invention may include two materials as disclosed herein. The first material: Material 1, is a flexible TEFLON film containing an array of micrometer or nanometer-sized TEF- LON cones. The second material: Material 2, comprises a flexible TEFLON film containing on its surface an array of micrometer or nanometer-sized TEFLON cones with a coating on its surface.

In one embodiment, the invention provides one or more arrays of micro- or nanometer-sized structures on flexible TEFLON film. Specifically, cone shaped structures on flexible TEFLON film, which are created by using differentially etching of colloidal beads introduced on top TEFLON film and the TEFLON film underneath, leading to Material 1. The cones on TEFLON film are created using monolayer or multilayer of colloidal beads. The TEFLON cone arrays may be coated with other materials including metal, semiconductor, oxides and organic or inorganic compounds with an arbitrary thickness, leading to Material 2. The TEFLON cones may be created from few microns to few tenths of nanometers sized colloidal beads. The optical properties of the TEFLON cone arrays such as reflectivity and transmittance are controllable by changing the size of the cone, etching condition and coating. The hydrophilicity of the TEFLON cone array surfaces can be tuned by changing the size of the cone, etching condition and coating. The surface conductivity of TEFLON cone arrays can be tuned by coating with conductive materials. The TEFLON nanocone array surface created on flexible TEFLON film is applicable onto arbitrary surfaces even with complicated geometry.

In another embodiment, Material 1 is fabricated by introducing a monolayer of monodisperse polystyrene beads on top of the TEFLON film and etching them with a single step oxygen plasma treatment for a certain time. The diameter of the polystyrene beads that are initially deposited on the TEFLON film can vary from few micrometers to few tenths of nanometers and this parameter determine the cone diameter and the respective spacing between the top of the cones of Material 1. The power, the oxygen pressure and the time of etching can also be varied and this parameter will affect the aspect-ratio of the cones of Material 1. During exposure to the oxygen plasma, the polystyrene beads and the TEFLON film underneath are etched simultaneously and the nanocone structures are created on the TEFLON film. As disclosed herein, for example, results were obtained using polystyrene beads having a diameter of 0.75 micrometer with following oxygen plasma etching condition, a time of 5 min, an oxygen pressure of 200 mTorr and an etching power of 50 W. As disclosed herein, Material 1 looks whitish at the centimeter scale. Material 1 is bendable, which shows that the flexibility of the TEFLON film is not affected by the fabrication process. Material 1 consists of multiple oriented domains of hexagonally-packed nanocones. The characteristic dimension of single oriented domains is typically of several tens of micrometers. The array structure in a single oriented domain, may consist of hexagonally-packed nanocones. The nanocones have a homogeneous height of about 1 micrometer in this case. Generally speaking, the diameter, and the height of the cones of Material 1 can vary from few tenths of nanometer to few micrometers.

In another embodiment, Material 1 is superhydrophobic with a measured contact angle of 157°.

In another embodiment, Material 2, is obtained by coating the surface of Material 1, on the side where the cones are. The coating is performed in order to add a specific physico-chemical characteristic or functionality to Material 1. The coating can be a conductor, a semiconductor, an insulator, a molecular layer or a hybrid material. The coating can be performed using physical vapor, chemical vapor deposition, layer by layer assembly, electroless deposition, polymerization, spin coating, spraying, molecular self-assembly or a combination of those techniques. The coating thickness can vary from few angstroms to few micrometers. As disclosed herein, for example, results were obtained using polystyrene beads having a diameter of 0.75 micrometer, oxygen plasma etching parameters of 5 min/200 mTorr/50 W and with a 50 nanometer-thick gold coating. As disclosed herein, Material 2 looks matte-black at the centimeter scale and is bendable, which shows that Material 2 absorb the light and that the flexibility of the TEFLON film is not affected by the fabrication process. The Material 2 is conductive with a measured conductivity of 22 mS·cm$^{-1}$. Due to the deposition of the gold layer, Material 2 has a higher the surface roughness with respect to Material 1 but the nanocone structure is retained.

In another embodiment, Material 1 is highly hydrophobic with a measured contact angle of 145°. Material 2 is highly anti-reflective and absorbing in a wide-angle and broad visible wavelength range (450-900 nm) with a low reflectivity below 1.0%.

Example 5

Generally

Arrays of nanostructures organized on surfaces are interesting because they provide excellent surface properties such as: superhydrophobicity, anti-reflectivity, enhanced catalytic activity, surface plasmon resonance activity, which are essential for very important applications including biosensors, solar cells, self-cleaning surfaces and anti-reflective coating. A technology to functionalize desired surfaces with these nanostructures is urgently demanded for medical diagnostics, energy industries and military industries and even for everyday life objects (for example, car, clothes, etc.). The problem is that these objects have various and complex shapes, and thus, their coating with such ordered nanostructures is currently difficult since it requires the use of very costly and time consuming technologies.

The processes which are most of the time used consist in generating the nanostructures of interest directly on the object. Such approaches generally involve focused ion beam fabrication (FIB), lithographically patterned nanofabrication (e.g. lithographically patterned electrodeposition), or the self-assembly of nanostructures (e.g. nanosphere lithography). However, fabrication processes based on FIB are very fastidious and time-consuming since all the nanofeatures have to be fabricated one after the other. Thus, this approach is not appropriate for patterning large surfaces. Lithographically patterned modification is more easily implemented on larger surfaces but requires multi steps and light-sensitive photoresist coatings. The use of nanostructure self-assemblies (such as nanosphere lithography) is an alternative that can be used for modifying large areas, however, the chemistry and the hydrophilicity of the substrate surface and the nanostructures have to be adjusted in order to allow the self-assembly to proceed properly, which makes the process non-versatile.

As described herein, the inventors developed a fabrication process for arrays of nanostructures on flexible polymer films that may be implemented in mass fabrication processes. In the fabrication method, the nanostructures may be created on a large scale on a flexible polymer film by a two-step process. The first step may include self-assembling a layer of micro- or nanoparticles on the polymer film. The second step may include modifying or etching the unprotected part of the polymer film. The fabricated nanostructured arrays can then be coated by a thin film of any deposable material that can be coated on the polymer (metal, polymer, oxide, semiconductor). The resulting nanostructured film is flexible and can be readily used for coating the surface of objects, even with complex shapes.

In accordance with various embodiments herein, some features are: i) the flexibility of the nanostructured films, ii) the easy implementation of the process, iii) the cheapness of the process, which does not require complicated and expensive equipments, iv) its versatility in terms of material (all the materials that can be coated on the polymer films are accessible) and v) the speed of the process.

In accordance with one embodiment, the inventors demonstrated the fabrication of nanostructured array on flexible TEFLON film by introducing polystyrene beads layers on top of the TEFLON film and etching them with single step oxygen plasma treatment. Results show that various nanostructures such as nanocones, nanocups, nanopyramids and nanocavities can be fabricated on the TEFLON film by optimizing the experimental parameters. Metal coatings of the fabricated nanostructures with gold, silver or nickel thin film (thickness about 20 to 70 nm) have been obtained and silver and nickel have been succeeded by thermal vapor deposition of metal thin films without distinguishable deformation of the nanostructures.

In one embodiment, gold nanocone arrays with a diameter of about 0.75 µm may be fabricated. For example, as described herein, a colloidal monolayer is formed on top of flexible TEFLON film by spincoating a solution of polystyrene (PS) beads with a diameter of 0.75 µm. After drying the solvent, the PS beads assemble hexagonal packed arrays on the TEFLON film. The surface is then etched by oxygen plasma. During exposure to the oxygen plasma, the PS beads and the TEFLON film underneath are etched simultaneously and the nanocone structures are created on the TEFLON film. For a short etching time (3 min), a hybrid structure consisting of shrunk PS beads and TEFLON nanopillars is created). As the etching time increases, the PS beads decrease and the heads of nanopillars sharpen. As further illustrated herein, for 6 minutes of etching, shows that only small PS residues remained on the top of nanocones. Finally, the TEFLON nanocones are coated with a thin gold layer (50 nm thick) by thermal evaporation. As it can be observed on these SEM images, the surface roughness increases after the gold evaporation but the nanocones structure is retained. One can note that the flexibility of the TEFLON film is retained after the fabrication process.

In accordance with various embodiments herein, the present invention is faster and less expensive than the nanofabrication processes based on FIB. It allows large surfaces to be nanostructured in a matter of minutes. It can also be faster and more robust than the lithographically patterned nanofabrication techniques since it can be a two-step process which does not require the use of clean rooms or light sensitive coatings. In accordance with various embodiments herein, the invention is more versatile than previous technologies based on self-assemblies, because they were directly applied on the surface of the object, and thus were limited to small areas, flat surfaces and surfaces with an appropriate surface chemistry. The flexible nanostructured films produced by the inventors can be readily used for coating objects regardless of shape, surface chemistry or hydrophobicity.

In another embodiment, the invention may exhibit hydrophobicity of the flexible nanocone array films, which could be used for the coating of food packaging, fridges, medical equipment, clothes, windows or walls. In another embodiment, the optical properties of such films may be controlled with the optical properties as a function of materials and geometries. This may include i) fabrication of anti-reflective surfaces in the infrared for invisibility against thermal cameras and reflector sights, ii) fabrication of disposable plasmonic biosensor chip for Surface Enhanced Raman Scattering (SERS) spectroscopy or surface plasmon enhanced fluorescence spectroscopy for clinical applications such as medical diagnostics, and iii) solar cell applications as effective light trapping and self-cleaning surfaces. The fabrication process may be further optimized in order to increase the surface that can be structured (for example, using a Langmuir Blodgett technique or Doctor blade technology) toward mass fabrication of the functionalized films.

Example 6

Additional Results

MicroRNAs (miRNAs) are small RNA molecules (19-23 base pair sequences) that are responsible for regulating gene translation. They work by catalyzing cleavage of messenger RNA (mRNA) or by directly binding to semi-complimentary, non-translating regions of mRNA to block translation. In recent years miRNAs have been discovered to play key roles in the pathogenesis of several types of human illnesses such as cancers, heart diseases, and neurodegenerative diseases. Researchers are currently studying these miRNAs as possible biomarkers of these diseases. Since miRNAs are only present in picomolar concentrations in biological systems, it is important to develop a sensitive method to detect these small quantities. Microarray-based techniques are particularly attractive for miRNA profiling as they are capable of screening large numbers of miRNAs simultaneously.

Two-dimensional, periodic nanocone arrays on flexible TEFLON films have been fabricated using a combination of colloidal lithography and oxygen plasma etching. This is a simple fabrication scheme that produces nanocone arrays on the centimeter scale in one single etching step. These TEFLON nanocone arrays exhibit unique optical properties that can potentially be translated into biosensing applications. After depositing a thin layer of plasmonic material (e.g. gold nanoparticles) on top of the nanocone arrays, the color of the sample turns to matte black indicating that the film has broadband anti-reflectivity and light absorption properties. Optical measurements show that the gold-coated nanocone arrays exhibit very low reflectivity (<1%) and strong absorption (~90%) throughout the visible wavelength range (450-900 nm). These nanocone arrays also exhibit unique superhydrophobic properties which make them particularly easy to functionalize into biosensor arrays.

Figure 20:
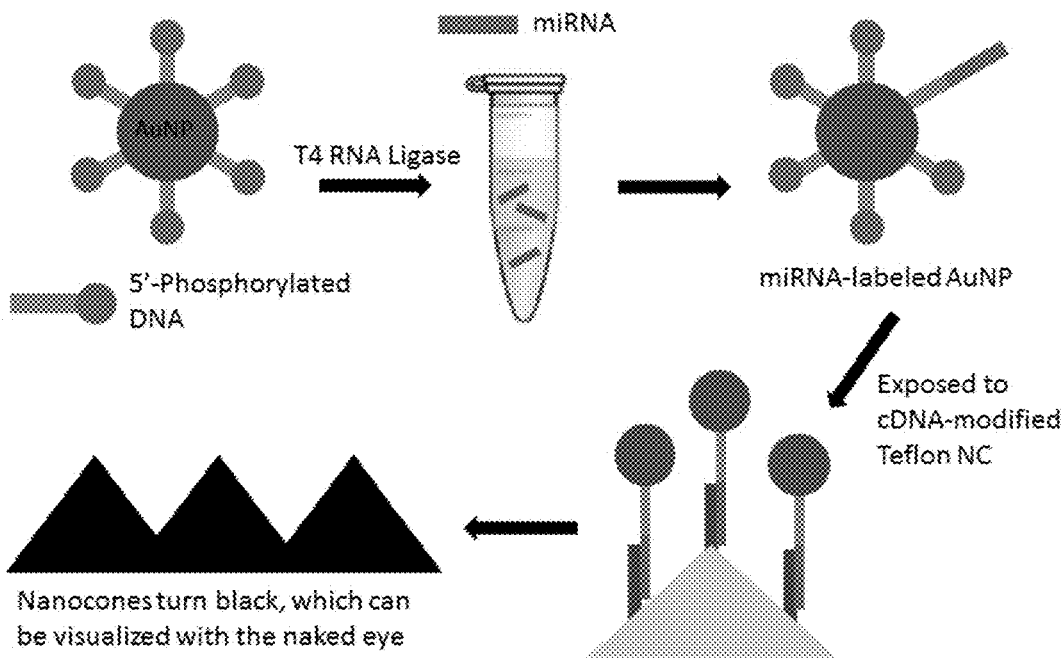
FIG. 20 depicts, in accordance with various embodiments herein, a schematic of microRNA (miRNA) detection using gold nanoparticles (AuNPs) on TEFLON nanocone array surfaces, which can be visualized with the naked eye.

Using a multiplexed nanoparticle-assisted detection scheme on complementary (cDNA)-modified TEFLON nanocone array surfaces, in one embodiment, the present invention provides a biosensor that will undergo a color change (light grey to black) when miRNAs bind on the nanocone surface. The biosensing scheme is illustrated in FIG. 20 herein. Gold nanoparticles (AuNPs) that are functionalized with phosphorylated ssDNA are used in conjunction with T4 RNA ligase to capture various miRNA from a target solution. Then, the miRNA-modified AuNPs are specifically adsorbed to the cDNA attached to the TEFLON nanocone array. Due to their broadband anti-reflectivity and strong light absorption properties, the TEFLON nanocone arrays will turn black upon complementary binding between the miRNA-modified AuNP and the correct cDNA attached to the surface. The color change can be visualized with the naked eye, making this miRNA detection method easy to implement.

As further disclosed herein, the inventors have demonstrated that 1) they have developed the appropriate surface chemistry to attach single-stranded DNA (ssDNA) on the nanocone surface; 2) one could set up a microarray format on the nanocone surface for detection of multiple miRNAs simultaneously; 3) complementary binding between ssDNA-modified AuNPs and the ssDNA-modified nanocone surface turned the surface black, which could be easily visualized with the naked eye.

Figure 21:
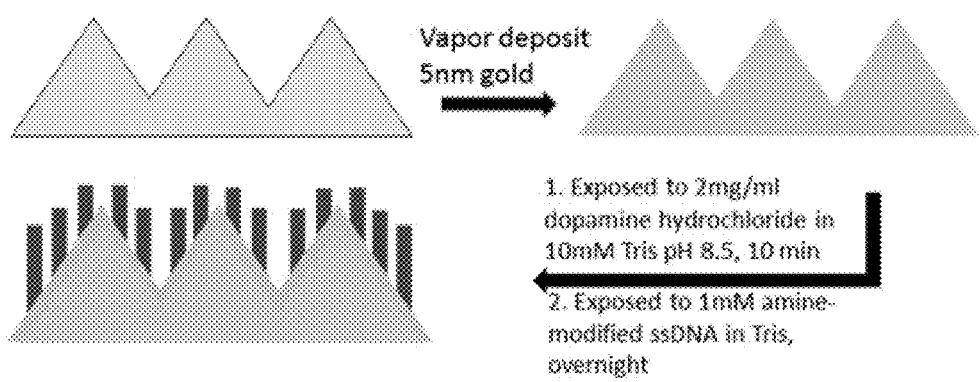
FIG. 21 depicts, in accordance with various embodiments herein, a schematic of the attachment of single-stranded DNA (ssDNA) onto the TEFLON nanocone surface.

Attachment of ssDNA on the TEFLON Nanocone Surface:

The process to attach ssDNA onto the TEFLON nanocone surface is outlined in FIG. 21 herein. A very thin layer of gold (5 nm) was vapor deposited onto the TEFLON nanocone surface using a thermal evaporator. The gold-coated nanocone surface was exposed to a 2 mg/ml dopamine solution in 10 mM Tris (pH 8.5) for 10 minutes, then rinsed with water and dried under nitrogen. This formed a layer of polydopamine (PDA), about 1.0 nm thick, on the nanocone surface. The PDA-coated nanocone surface was exposed to 250 μM amine-modified ssDNA in Tris buffer for about 12 hours to immobilize the ssDNA on the nanocone surface, then rinsed with water and dried under nitrogen.

Figure 22:
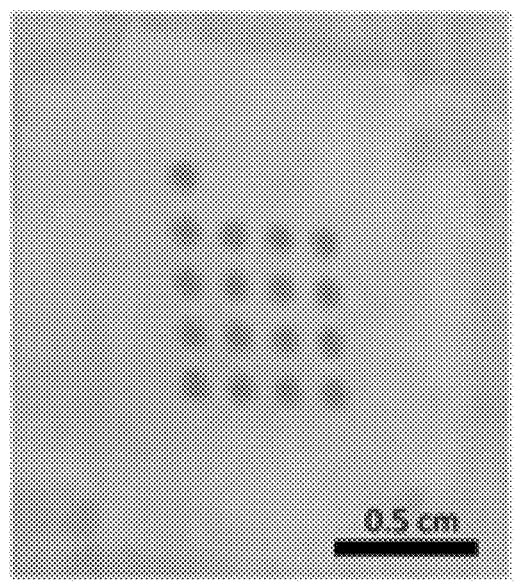
FIG. 22 depicts, in accordance with various embodiments herein, 5 nm of gold was selectively vapor deposited onto various areas of the TEFLON nanocone surface, creating grey spots. Above is a TEFLON nanocone surface set up in a 17-spot microarray format.

Microarray Format for miRNA Profiling:

5 nm of gold was deposited onto different areas of the TEFLON nanocone surface using a thermal evaporator, creating grey spots. The inventors successfully created a 17-spot array on the nanocone surface, where one could detect up to 17 different miRNA simultaneously (FIG. 22).

Figure 23:
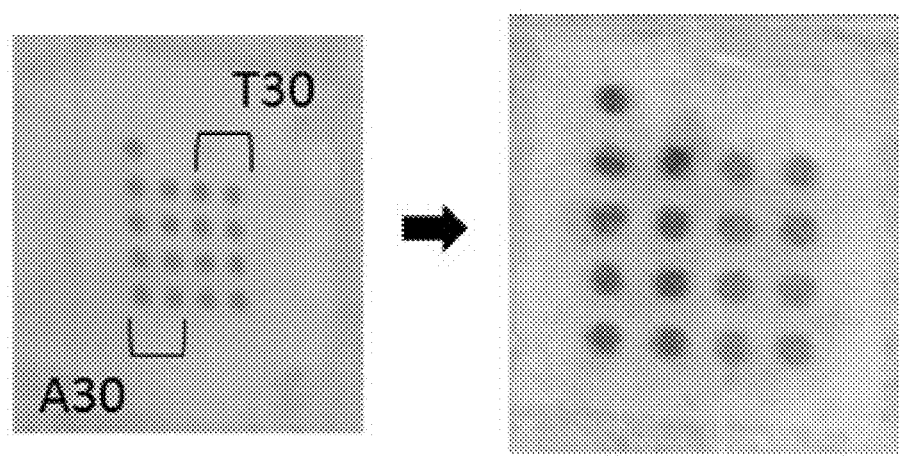
FIG. 23 depicts, in accordance with various embodiments herein, A30 and T30 ssDNA were selectively attached onto different spots of the TEFLON nanocone microarray. After exposing to a solution containing T30-modified AuNPs, complementary binding occurred at the A30 spots, causing them to turn black.

Complementary Binding Turned the TEFLON Nanocone Surface to Black:

Two types of ssDNA, A30 and T30, were attached onto the TEFLON nanocone surface (FIG. 4a). The entire TEFLON nanocone surface was exposed to a solution containing T30-modified AuNPs for 10 minutes, then rinsed with water and dried under nitrogen. It was observed that when the T30-modified AuNPs bound to A30-TEFLON nanocones, complementary binding turned the nanocone surface black. The T30-TEFLON nanocones did not turn black because the T30-modified AuNPs did not bind there (FIG. 23b.)

As disclosed herein, the inventors demonstrate the potential of the TEFLON nanocone array surface as a novel, easy-to-make biosensor that can simultaneously detect multiple miRNAs. Since detection can be visualized with the naked eye, no additional instruments are necessarily needed. This makes the TEFLON nanocone surface a portable device suitable for field testing in developing nations, and can greatly advance global health efforts. In another embodiment, the technology may be adopted for other non-diseases sensing applications, such as detection of bacteria in contaminated water supply or pathogens in crops.

Example 7

MicroRNA Profiling Using TEFLON Nanocone Array Surfaces

MicroRNAs (miRNAs) are small RNA molecules (19-23 base pair sequences) that are responsible for regulating gene translation. They work by catalyzing cleavage of messenger RNA (mRNA) or by directly binding to semi-complimentary, non-translating regions of mRNA to block translation. In recent years, miRNAs have been discovered to play key roles in the pathogenesis of several types of human illnesses such as cancers, heart diseases, and neurodegenerative diseases. Since miRNAs are only present in picomolar concentrations in biological systems, it is important to have a sensitive method to detect these small quantities. Microarray-based techniques are particularly attractive for miRNA profiling as they are capable of screening large numbers of miRNAs simultaneously.

Two-dimensional, periodic nanocone arrays on flexible TEFLON films were fabricated using a combination of colloidal lithography and oxygen plasma etching. This is a simple fabrication scheme that produces nanocone arrays on the centimeter scale in one single etching step. These TEFLON nanocone arrays exhibit unique optical properties that can potentially be translated into biosensing applications. After depositing a thin layer of plasmonic material (e.g. gold nanoparticles) on top of the nanocone arrays, the color of the sample turns to matte black indicating that the film has broadband anti-reflectivity and light absorption properties. Optical measurements show that the gold-coated nanocone arrays exhibit very low reflectivity (<1%) and strong absorption (~90%) throughout the visible wavelength range (450-900 nm). These nanocone arrays also exhibit unique superhydrophobic properties which make them particularly easy to functionalize into biosensor arrays.

Using a multiplexed nanoparticle-assisted detection scheme on complementary DNA (cDNA)-modified TEFLON nanocone array surfaces, in one embodiment, the present invention provides a biosensor that will undergo a color change (light grey to black) when miRNAs bind on the nanocone surface. Gold nanoparticles (AuNPs) that are functionalized with phosphorylated ssDNA are used in conjunction with T4 RNA ligase to capture various miRNA from a target solution. Then, the miRNA-modified AuNPs are specifically adsorbed to the cDNA attached to the TEFLON nanocone array. Due to their broadband anti-reflectivity and strong light absorption properties, the TEFLON nanocone arrays will turn black upon complementary binding between the miRNA-modified AuNP and the correct cDNA attached to the surface. The color change can be visualized with the naked eye, making this miRNA detection method easy to implement. As further disclosed herein, the inventors demonstrated that 1) they have developed the appropriate surface chemistry to attach single-stranded DNA (ssDNA) on the nanocone surface; 2) one can set up a microarray format on the nanocone surface for detection of multiple miRNAs simultaneously; 3) complementary binding between ssDNA-modified AuNPs and the ssDNA-modified nanocone surface turned the surface black, which could be easily visualized with the naked eye.

Some Benefits:
    Low cost, easy-to-make TEFLON nanocones biosensor
    Potentially leading to earlier diagnosis of diseases such as cancer, heart diseases, neurodegenerative diseases
    Can profile several miRNAs simultaneously
    Detection can be visualized with the naked eye
    Additional instrumentation is unnecessary
    Portable device
    Detection is fast and simple
    Suitable for use in rural areas or developing nations
    Advance global health efforts
    Other non-disease applications:
    Water contaminants
    Pathogens in food
Overall:
    miRNAs play key roles in pathogenesis of a variety of diseases
    Simple fabrication of TEFLON nanocone array surfaces Unique optical properties of TEFLON nanocone surfaces for biosensing applications Detection can be visualized with the naked eye Developed method to attach ssDNA on TEFLON nancones PDA layer, then amine-modified ssDNA Binding specificity confirmed Microarray pattern on TEFLON nanocone surfaces to detect multiple ssDNA simultaneously Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of fabricating an array of nanostructures on a flexible Fluorinated Ethylene Propylene (FEP) film, comprising:
    self-assembling a layer of particles on the FEP film; and
    fabricating an array of nanostructures by simultaneously etching the layer of particles and the FEP film.

2. The method of claim 1, wherein the array of nanostructures are further coated by an additional film.

3. The method of claim 1, wherein the etching fabricates cone shaped nanostructures.

4. The method of claim 1, wherein the layer is a monolayer or multilayer.

5. The method of claim 3, wherein the cone shaped structures are fabricated by differentially etching the layer of particles, and wherein the layer of particles comprises colloidal beads.

6. The method of claim 1, further comprising adjusting surface conductivity of the array of nanostructures by coating the array of nanostructures with conductive materials.

7. The method of claim 1, wherein the nanostructures include nanocups, nanopyramids and/or nanocavities.

8. The method of claim 1, wherein the particles comprise colloidal beads or polystyrene beads.

9. The method of claim 1, wherein the size of the particles in the self-assembling step determine the size of the nanostructures on the flexible FEP film.

10. The method of claim 1, wherein the flexible FEP film has a first side and a second side, and the array of nanostructures are fabricated on both the first and second sides of the flexible FEP film.

* * * * *